US011311276B2

(12) United States Patent
Shikama (10) Patent No.: US 11,311,276 B2
(45) Date of Patent: Apr. 26, 2022

(54) ULTRASONIC DIAGNOSTIC APPARATUS AND IMAGE SYNTHESIS METHOD

(71) Applicant: Konica Minolta, Inc., Tokyo (JP)

(72) Inventor: Jo Shikama, Machida (JP)

(73) Assignee: KONICA MINOLTA, INC., Tokyo (JP)

( * ) Notice: Subject to any disclaimer, the term of this patent is extended or adjusted under 35 U.S.C. 154(b) by 417 days.

(21) Appl. No.: 15/699,508

(22) Filed: Sep. 8, 2017

(65) Prior Publication Data

US 2018/0085093 A1 Mar. 29, 2018

(30) Foreign Application Priority Data

Sep. 29, 2016 (JP) .............................. JP2016-191698

(51) Int. Cl.
*A61B 8/08* (2006.01)
*A61B 8/00* (2006.01)
(Continued)

(52) U.S. Cl.
CPC .............. *A61B 8/5207* (2013.01); *A61B 8/14* (2013.01); *A61B 8/54* (2013.01); *G01S 15/89* (2013.01); *A61B 8/4405* (2013.01)

(58) Field of Classification Search
CPC ....... A61B 8/14; A61B 8/4405; A61B 8/5207; A61B 8/54; G01S 15/89; G01S 15/8977; G01S 15/8995
See application file for complete search history.

(56) References Cited

U.S. PATENT DOCUMENTS 6,017,313 A * 1/2000 Bratteli .................. A61B 5/021
600/481
6,511,426 B1 * 1/2003 Hossack ............... G01S 15/899
600/437
(Continued)

FOREIGN PATENT DOCUMENTS

JP 3935433 B2 3/2007

OTHER PUBLICATIONS

Weighted regression—worked example—MedCalc statistical . . . www.medcalc.org > . . . > Statistics menu > Regression Jun. 21, 2014—Weighted regression—worked example. The problem of heteroscedasticity. (Year: 2014).*

*Primary Examiner* — Pascal M Bui Pho
*Assistant Examiner* — Alexei Bykhovski
(74) *Attorney, Agent, or Firm* — Lucas & Mercanti, LLP (57) ABSTRACT

An ultrasonic diagnostic apparatus includes an image generating unit configured to generate a plurality of different ultrasound image data items from reception signals corresponding to a plurality of different steering angles, on the basis of the reception signals which an ultrasound probe has generated on the basis of reflected ultrasonic waves received from a reflecting surface of a subject body by transmitting ultrasonic waves at the plurality of different steering angles, and a regression estimate generating unit configured to perform regression analysis on the basis of the different steering angles and the ultrasound image data items, and generate regression estimates which are weighting values on the basis of the result of the regression analysis, and an image synthesis unit configured to perform weighting on the plurality of ultrasound image data items on the basis of the regression estimates, and synthesize them, thereby generating synthetic image data.

10 Claims, 8 Drawing Sheets

(51) Int. Cl.
  *A61B 8/14* (2006.01)
  *G01S 15/89* (2006.01)

(56) References Cited

U.S. PATENT DOCUMENTS

| | | | |
|---|---|---|---|
| 6,547,732 B2* | 4/2003 | Jago | G01S 7/52036 600/437 |
| 10,003,768 B2* | 6/2018 | Adsumilli | H04N 7/0137 |
| 2014/0046187 A1* | 2/2014 | Taniguchi | A61B 8/5269 600/444 |
| 2014/0073937 A1* | 3/2014 | Rodriguez-Llorente | G06K 9/00496 600/476 |

* cited by examiner

ULTRASONIC DIAGNOSTIC APPARATUS AND IMAGE SYNTHESIS METHOD

CROSS-REFERENCE TO RELATED APPLICATIONS

Japanese Patent Application No. 2016-191698 filed on Sep. 29, 2016 including description, claims, drawings, and abstract the entire disclosure is incorporated herein by reference in its entirety.

BACKGROUND

Technological Field

The present invention relates to an ultrasonic diagnostic apparatus and an image synthesis method.

Description of the Related Art

In the related art, there is a known ultrasonic diagnostic apparatus which has an ultrasound probe having an array of a number of vibrators, and performs transmission and reception of ultrasonic waves with respect to a subject body such as a biological body, and generates ultrasound image data on the basis of signals obtained from received ultrasonic waves, and displays an ultrasound image based on the ultrasound image data on an image display device. Ultrasound image diagnosis using such an apparatus is performed by an easy operation, that is, by just putting the ultrasound probe on the surface of a subject body, whereby it is possible to obtain the aspects of heartbeats, fetal movement, and so on in real time, and since the apparatus is non-invasive and safe, it is possible to repeatedly perform ultrasound image diagnosis.

However, images which are acquired by such an ultrasonic diagnostic apparatus include not only information on tissues in subject bodies but also a variety of noise and speckles caused by interference of reception signals obtained from ultrasonic waves received by the ultrasound probe, and these speckles often disturb correct understanding of the positions and shapes of the boundaries of the tissues in the subject bodies.

Recently, for example, ultrasonic diagnostic apparatuses using a spatial compounding method as a processing method for reducing noise and speckles as described above have been spread. The spatial compounding method is a method of performing transmission and reception of ultrasonic waves in a plurality of different directions with respect to the same part of a subject body in the same period, thereby obtaining a plurality of ultrasound image data items, and averagely superimposing them. For example, in a case where data items on N-number of ultrasound images are acquired, the spatial compounding method can be used to synthesize the data items such that the synthetic image data has noise and speckles reduced in proportion to the square root of N.

Also, according to the spatial compounding method, it is possible to improve anisotropic-part extracting performance. An anisotropic part is a part which causes reception signals having different intensities depending on angles by scattering, reflecting, and the like if ultrasonic waves reach the corresponding part, specifically, a part of soft tissue which does not have reflection intensity stronger than that of the surfaces of bones but has a specular reflection characteristic, for example, a tendon or a ligament in skeletal muscles of a subject body.

For example, Patent Document 1 discloses a technology for making an ultrasonic diagnostic apparatus using spatial compounding method as described capable of generating a higher-quality image by obtaining ultrasound images on the basis of reflected signals from a plurality of directions and synthesizing the average values, maximum values, minimum values, median values, and the like of individual pixel values of the ultrasound images in accordance with a control signal selected on the basis of the type of a diagnostic test.

[Patent Document 1] Japanese Patent No. 3935433

In a case where ultrasonic waves transmitted from a probe (an ultrasound probe) are reflected from body tissues in a subject body, in general, the intensities of signals reflected from body tissues which face the ultrasound probe (body tissues whose reflecting surfaces are perpendicular to the transmission direction of ultrasonic waves) are stronger than the intensities of signals reflected from body tissues which do not face the ultrasound probe (body tissues whose reflecting surfaces are not perpendicular to the transmission direction of ultrasonic waves). For this reason, in some ultrasonic diagnostic images generated on the basis of reflected-wave signals of ultrasonic waves, parts corresponding to body tissues which do not face the ultrasound probe are unclearer than parts corresponding to body tissues which face the ultrasound probe.

For example, in the technology disclosed in Patent Document 1, if pixel values are amplified by synthesizing maximum values of pixel values, it is possible to amplify signals reflected from body tissues which do not face the ultrasound probe. Therefore, it is possible to image body tissues which do not face the ultrasound probe relatively clear. However, since other signals received by the ultrasound probe, i.e. for example, signals reflected from body tissues facing the ultrasound probe, signals including speckle noise, and the like are also amplified, unnatural images may be obtained.

SUMMARY

An object of the present invention is to provide an ultrasonic diagnostic apparatus and an image synthesis method capable of appropriately generating ultrasound images including body tissues which do not face an ultrasound probe.

To achieve the above-mentioned object, according to an aspect, an ultrasonic diagnostic apparatus reflecting one aspect of the present invention comprises: an image generating unit configured to generate a plurality of different ultrasound image data items from reception signals corresponding to a plurality of different steering angles, respectively, on the basis of the reception signals which an ultrasound probe has generated on the basis of reflected ultrasonic waves received from a reflecting surface of a subject body by transmitting ultrasonic waves at the plurality of different steering angles; a regression estimate generating unit configured to perform regression analysis on the basis of the plurality of different steering angles, and the plurality of ultrasound image data items corresponding to the plurality of different steering angles, and generate regression estimates which are predetermined weighting values on the basis of the result of the regression analysis; and an image synthesis unit configured to perform weighting on the plurality of ultrasound image data items on the basis of the regression estimates, and synthesize them, thereby generating a synthetic image data item.

BRIEF DESCRIPTION OF THE DRAWING

The advantages and features provided by one or more embodiments of the invention will become more fully

DETAILED DESCRIPTION OF EMBODIMENTS

Hereinafter, one or more embodiments of the present invention will be described with reference to the drawings. However, the scope of the invention is not limited to the disclosed embodiments.

Hereinafter, an ultrasonic diagnostic apparatus according to an embodiment of the present invention will be described with reference to the accompanying drawings. However, the scope of the invention is not limited to examples shown in the drawings. Also, in the following description, components having the same functions and configurations are denoted by the same reference symbols, and repeated descriptions thereof are avoided.

Figure 1:
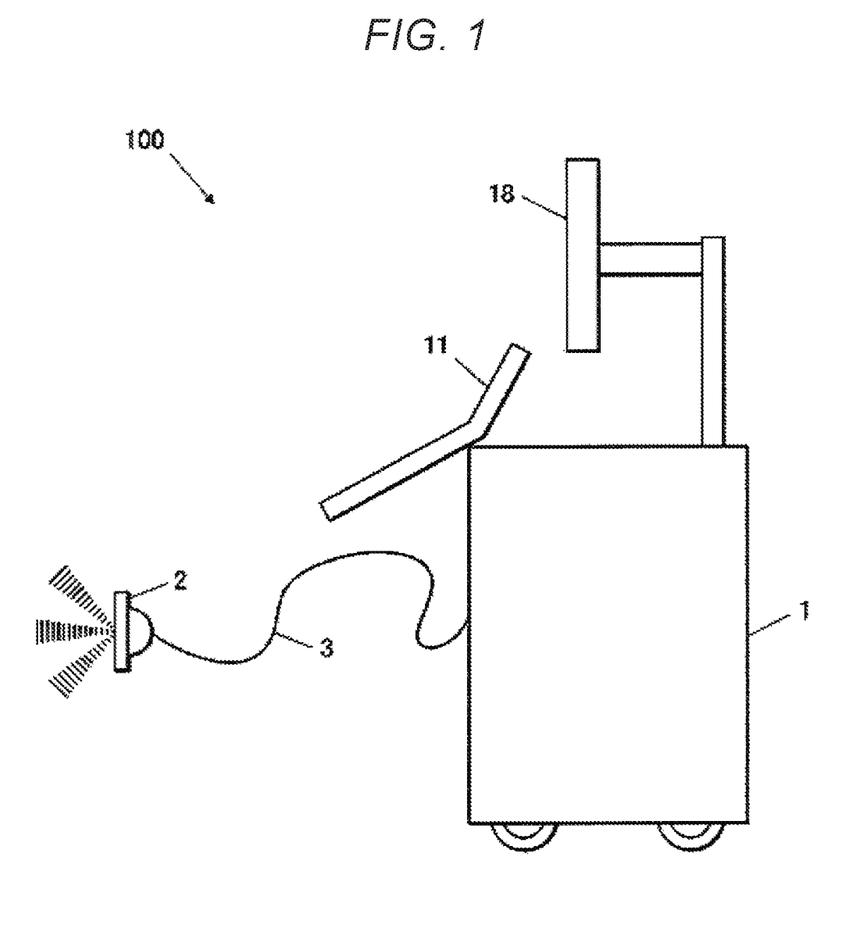
FIG. 1 is a view illustrating an example of the configuration of an ultrasonic diagnostic apparatus.

FIG. 1 is a view illustrating an example of the configuration of an ultrasonic diagnostic apparatus 100. As shown in FIG. 1, the ultrasonic diagnostic apparatus 100 has an ultrasonic diagnostic apparatus body 1 and an ultrasound probe 2. The ultrasound probe 2 transmits ultrasonic waves (ultrasonic transmission waves) into a subject body such as a biological body (not shown in the drawings), and receives reflected waves (reflected ultrasonic waves (echoes)) of the ultrasonic waves from the inside of the subject body.

The ultrasonic diagnostic apparatus body 1 is connected to the ultrasound probe 2 by a cable 3, and transmits an electric signal as a drive signal to the ultrasound probe 2, thereby controlling the ultrasound probe 2 such that the ultrasound probe transmits ultrasonic transmission waves toward a subject body. Then, if the ultrasound probe 2 receives reflected waves from the inside of the subject body, and the ultrasound probe 2 generates electric signals as reception signals, the ultrasonic diagnostic apparatus body images the internal state of the subject body as an ultrasound image on the basis of the reception signals.

The ultrasound probe 2 has vibrators 2a (see FIG. 2) composed of a plurality of piezoelectric elements, and the plurality of vibrators 2a is arranged in a one-dimensional array in an azimuth direction (a scan direction). The number of vibrators 2a can be arbitrarily set.

Figure 2:
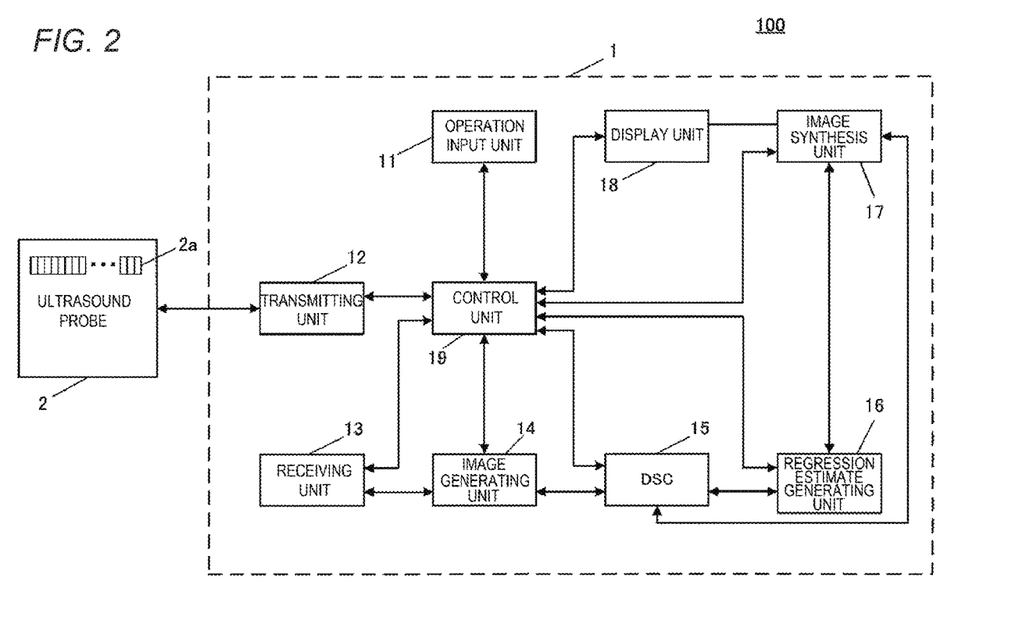
FIG. 2 is a block diagram illustrating an example of the configuration of an ultrasonic diagnostic apparatus body.

FIG. 2 is a block diagram illustrating an example of the configuration of the ultrasonic diagnostic apparatus body 1. As shown in FIG. 2, the ultrasonic diagnostic apparatus body 1 has, for example, an operation input unit 11, a transmitting unit 12, a receiving unit 13, an image generating unit 14, a digital scan converter (DSC) 15, a regression estimate generating unit 16, an image synthesis unit 17, a display unit 18, and a control unit 19.

The operation input unit 11 is an operation device for performing inputting and the like of, for example, a command to instruct diagnosis start, data such as personal information of subject bodies, and various parameters for displaying ultrasound images on the display unit 18, and is specifically various switches, buttons, a trackball, a mouse, a keyboard, and the like. The operation input unit 11 outputs operation signals based on input operations to the control unit 19.

The transmitting unit 12 is a circuit configured to supply an electric signal as a drive signal to the ultrasound probe 2 through the cable 3 under the control of the control unit 19, thereby controlling the ultrasound probe 2 such that the ultrasound probe generates ultrasonic transmission waves. The transmitting unit 12 includes, for example, a clock generating circuit, a delay circuit, and a pulse generating circuit (not shown in the drawings). The clock generating circuit is a circuit configured to generate a clock signal to determine drive signal transmission timings and transmission frequencies. The delay circuit is a circuit configured to set a delay time for each individual path corresponding to each vibrator 2a to delay drive signal transmission by the set delay time and perform focusing of transmission beams composed of ultrasonic transmission waves (transmission beam forming) and setting of angles of transmission beams (steering). The pulse generating circuit is a circuit configured to generate a pulse signal as a drive signal with a predetermined cycle.

The transmitting unit 12 configured as described above, for example, drives some (for example, several tens of) consecutive vibrators of the plurality of (for example, a hundred and several tens to two hundreds and several tens of) vibrators 2a arranged in the ultrasound probe 2 to generate ultrasonic transmission waves. Further, the transmitting unit 12 performs scanning by performing switching to some vibrators 2a to be driven in the azimuth direction for generating each ultrasonic transmission wave. Also, the transmitting unit 12 can perform scanning while changing the angle of a transmission beam, thereby capable of receiving a plurality of reflected signals having different angles.

The receiving unit 13 is a circuit configured to receive electric signals as reception signals from the ultrasound probe 2 through the cable 3 under the control of the control unit 19. The receiving unit 13 includes, for example, an amplifier, an A/D conversion circuit, and a phasing addition circuit. The amplifier is a circuit configured to amplify the reception signals by amplification factors predetermined for the paths corresponding to the vibrators 2a, respectively. The A/D conversion circuit is a circuit configured to perform analog/digital conversion (A/D conversion) on the amplified reception signals. The phasing addition circuit is a circuit configured to adjust the time phases of the reception signals subjected to the A/D conversion by applying delay times to the paths corresponding to the vibrators 2a, respectively, and add them (phasing addition), thereby generating sound ray data. In other words, the phasing addition circuit generates sound ray data by performing reception beam forming with respect to the reception signal of each vibrator 2a.

Under the control of the control unit 19, the image generating unit 14 performs an envelope detection process, logarithmic compression, and the like on the sound ray data input from the receiving unit 13 to adjust the dynamic range and the gain, and performs luminance conversion, thereby generating B-mode ultrasound image data. The B-mode ultrasound image data is data representing the intensities of the reception signals by luminance levels. Also, in the present embodiment, the image generating unit 14 may be able to generate A-mode image (amplitude image) data, M-mode image (motion image) data, and ultrasound image data based on a Doppler method, besides the B-mode ultrasound image data.

Also, in the present embodiment, in a case where the ultrasound probe 2 performs scanning by changing the angle as described above, the image generating unit 14 generates a plurality of ultrasound image data items on the basis of a plurality of reflected signals having different angles. The plurality of ultrasound image data items generated as described above overlap one another in a part or the whole of the scan area.

Under the control of the control unit 19, the DSC 15 performs scan frequency conversion on the plurality of ultrasound image data items generated by the image generating unit 14, and outputs the conversion results to the regression estimate generating unit 16.

Under the control of the control unit 19, the regression estimate generating unit 16 performs a regression analysis process of generating regression estimates by performing predetermined regression analysis on the plurality of ultrasound image data items output from the DSC 15 with respect to each pixel or each of predetermined areas, thereby calculating the regression estimates, and outputs the regression estimates to the image synthesis unit 17. Here, the regression estimates are values calculated on the basis of parameters obtained by regression analysis of the regression estimate generating unit 16. Details of the regression analysis process which is performed by the regression estimate generating unit 16 will be described below.

Under the control of the control unit 19, the image synthesis unit 17 performs an image synthesizing process of generating synthetic image data by performing synthesis on the overlapping part of the scan area on the basis of the regression estimates calculated by the regression estimate generating unit 16 and the plurality of ultrasound image data items output from the DSC 15, thereby generating the synthetic image data. Details of the image synthesizing process which is performed by the image synthesis unit 17 will be described below.

The display unit 18 is a display device such as a light-emitting diode (LED) display, a liquid crystal display (LCD), a cathode-ray tube (CRT) display, an organic EL (electronic luminescence) display, an inorganic EL display, and a plasma display. Under the control of the control unit 19, the display unit 18 displays ultrasound images on the basis of synthetic image data output from the image synthesis unit 17.

The control unit 19 has, for example, a central processing unit (CPU), a read only memory (ROM), and a random access memory (RAM), and reads out various processing programs such as a system program stored in the ROM, and develops them in the RAM, and performs centralized control on the operation of each unit of the ultrasonic diagnostic apparatus 100 according to the developed programs.

The ROM is configured with a non-volatile memory such as a semiconductor memory and so on, to store a system program corresponding to the ultrasonic diagnostic apparatus 100, various processing programs executable on the system program, a variety of data such as a gamma table, and the like. These programs are stored in the form of program codes readable by a computer, and the CPU sequentially performs operations according to the program codes. The RAM forms a work area for temporarily storing various programs to be executable by the CPU, and data relative to those programs.

Now, the regression analysis process which is performed by the regression estimate generating unit 16 will be described in detail. First, the relation between the angles of transmission beams of the ultrasound probe 2 of the ultrasonic diagnostic apparatus 100 of the present embodiment and the direction of a reflecting surface of body tissue in a subject body will be described.

Figure 3:
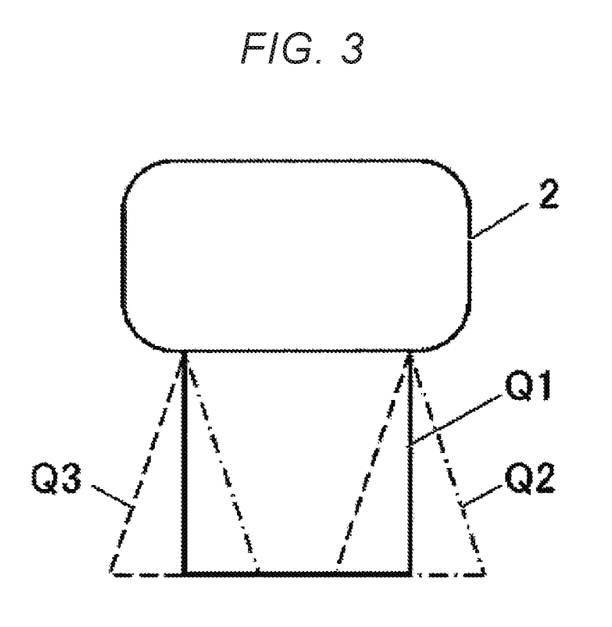
FIG. 3 is a view illustrating the relation between the angles of transmission beams which are transmitted from an ultrasound probe and operation areas.

FIG. 3 is a view illustrating the relation between the angles of transmission beams which are transmitted from the ultrasound probe 2 and operation areas. For example, as shown in FIG. 3, the ultrasonic diagnostic apparatus 100 sets the angle of a transmission beam to be output from the ultrasound probe 2, to a direction perpendicular to the azimuth direction, and performs scanning, thereby acquiring a component image data item of a scan area Q1. Also, in the present embodiment, the angle of a transmission beam which is output from the ultrasound probe 2 is referred to as the steer angle (the steering angle). More specifically, the steer angle is an angle which is formed by the central axis of the ultrasound probe 2 and the transmission direction of the ultrasonic beam.

Also, in a case of shifting the steering angle to each of the right and the left by a predetermined angle (for example, 10°) and performing scanning, the ultrasonic diagnostic apparatus 100 can acquire a component image data item of a scan area Q2 and a component image data item of a scan area Q3. The scan areas Q1 to Q3 overlap one another at least partially. Further, the ultrasonic diagnostic apparatus synthesizes the component image data items of the scan areas Q1 to Q3, thereby obtaining a synthetic image data item. The synthetic image data item obtained in the above-mentioned manner is an ultrasound image data item having noise and speckles reduced in proportion to the number of images synthesized as described above.

Also, in the example shown in FIG. 3, three component image data items obtained at the steering angles of 0°, +10°, or −10° are synthesized to generate a synthetic image. However, actually, it is preferable that the ultrasonic diagnostic apparatus 100 acquires more component image data items at more steering angles, and synthesizes them, thereby generating an ultrasound image data item.

Figure 4A:
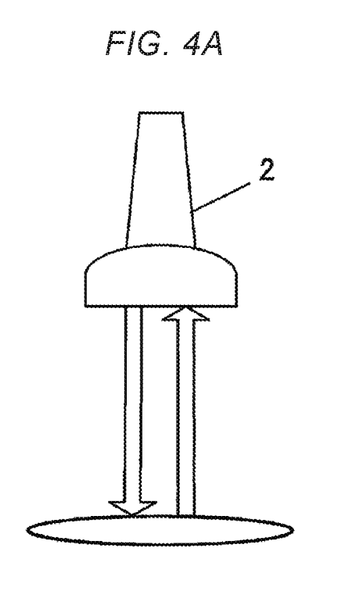
FIG. 4A is a view illustrating an example of a situation in which an ultrasonic beam is transmitted at a steering angle of 0° to a target facing the ultrasound probe.
Figure 4B:
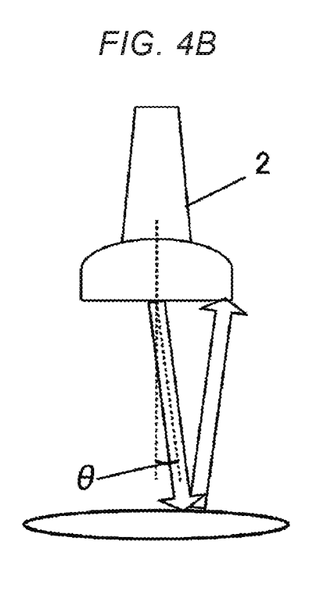
FIG. 4B is a view illustrating an example of a situation in which an ultrasonic beam is transmitted at a steer angle of $\theta$ ($\theta \neq 0$) to a target facing the ultrasound probe.

FIGS. 4A and 4B are views illustrating examples of ultrasonic transmission beams and reflected beams relative to body tissues facing the ultrasound probe 2. Body tissues facing the ultrasound probe 2 mean body tissues having reflecting surfaces forming 90° with the transmission direction of ultrasonic beams from the ultrasound probe 2. Also, hereinafter, scan object body tissues in subject bodies will be referred to as targets.

FIG. 4A is a view illustrating an example of a situation in which a transmission beam is transmitted at a steering angle of 0° toward a target facing the ultrasound probe 2, and FIG. 4B is a view illustrating an example of a situation in which a transmission beam is transmitted at a steer angle of θ (θ≠0) toward a target facing the ultrasound probe 2.

As shown in FIG. 4A, in the case where the steer angle is 0°, the ultrasound probe 2 can receive most of ultrasonic waves reflected from the target facing the ultrasound probe 2. Meanwhile, in the case where the steering angle is θ, as shown in FIG. 4B, the amount of reflected beams which the ultrasound probe 2 can receive is less than that in the case where the steer angle is 0° as shown in FIG. 4A. In other words, when a target faces the ultrasound probe 2, the intensities of reflected signals which the ultrasound probe 2 can receive in a case where the steering angle is θ are weaker than those in a case where the steer angle is 0°.

Figure 5A:
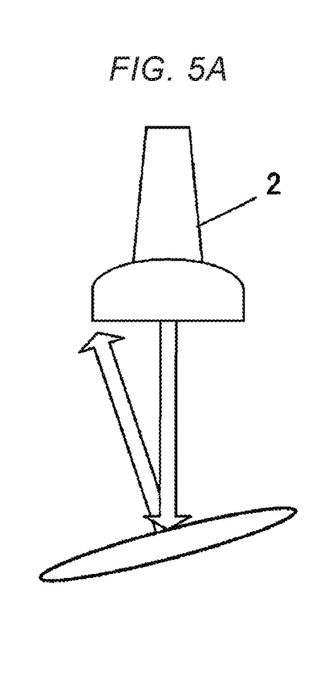
FIG. 5A is a view illustrating an example of a situation in which an ultrasonic beam is transmitted at a steer angle of 0° to a target which does not face an ultrasound probe 2.
Figure 5B:
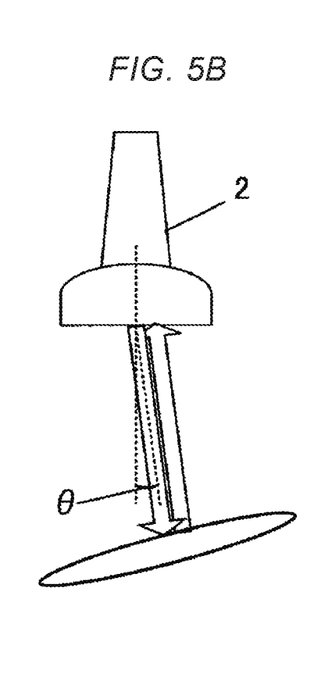
FIG. 5B is a view illustrating an example of a situation in which an ultrasonic beam is transmitted at a steer angle of $\theta$ ($\theta \neq 0$) to a target which does not face the ultrasound probe 2.

Meanwhile, FIGS. 5A and 5B are views illustrating examples of ultrasonic transmission beams and reflected beams relative to targets which do not face the ultrasound probe 2. FIG. 5A is view illustrating an example of a situation in which a transmission beam is transmitted at a steering angle of 0° toward a target which does not face the ultrasound probe 2, and FIG. 4B is a view illustrating an example of a situation in which a transmission beam is transmitted at a steer angle of θ (θ≠0) toward a target which does not face the ultrasound probe 2.

As shown in FIG. 5B, in a case where the inclination angle of the reflecting surface of the target relative to the direction of the transmission beam is substantially equal to the steering angle θ, the amount of reflected beams which the ultrasound probe 2 can receive is equal to that in the case where an ultrasonic beam is transmitted at the steer angle of 0° toward the target facing the ultrasound probe as shown in FIG. 4A. In other words, in the case where the inclination angle of the reflecting surface of the target relative to the direction of the transmission beam is substantially equal to the steering angle θ compared to the case where the ultrasonic beam is transmitted at the steer angle of 0° toward the target which does not face the ultrasound probe 2 as shown in FIG. 5A, the amount of reflected beams which the ultrasound probe 2 can receive becomes relatively large. In other words, when a target does not face the ultrasound probe 2, the intensities of reflected signals which the ultrasound probe 2 can receive in a case of transmitting the ultrasonic beam at a steer angle substantially equal to the inclination angle of the reflecting surface of the target relative to the direction of the transmission beam are relatively stronger than those in a case where the steer angle is 0°.

Also, hereinafter, a target facing the ultrasound probe 2 and a target which does not face the ultrasound probe 2 will be referred to as a facing target and a non-facing target, respectively.

Figure 6A:
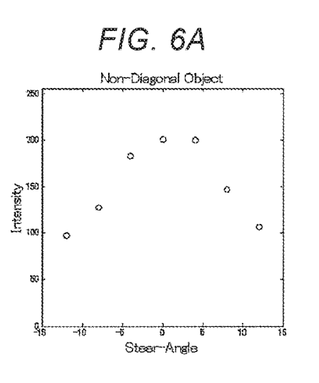
FIG. 6A is a view illustrating the relation between the intensities of reflected signals from a facing target and steer angles.
Figure 6B:
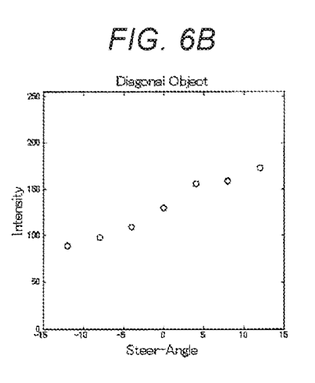
FIG. 6B is a view illustrating the relation between the intensities of reflected signals from a non-facing target and steer angles.
Figure 6C:
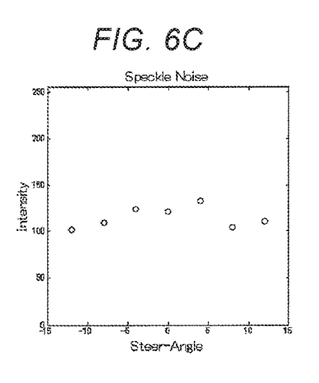
FIG. 6C is a view illustrating the relation between the intensities of reflected signals including speckle noise and steer angles.

FIGS. 6A to 6C are views illustrating examples of the relations between the intensities of reflected signals and steer angles. FIG. 6A shows the relation between the intensities of reflected signals from a facing target and steer angles, and FIG. 6B shows the relation between the intensities of reflected signals from a non-facing target and steer angles, and FIG. 6C shows the relation between the intensities of reflected signals including speckle noise and steer angles.

In a case of a facing target, as described with reference to FIGS. 4A and 4B, when the steer angle is 0°, the intensities of reflected signals are highest, and as the absolute value of the steer angle increases, the intensities of reflected signals decrease. FIG. 6A is a view illustrating the intensities of reflected signals from a facing target and steer angles in the same plane.

Meanwhile, in a case of a non-facing target, as described with reference to FIGS. 5A and 5B, if the inclination angle of the reflecting surface of the target relative to the direction of the transmission beam is +θ, as the steer angle gradually increases from an angle slightly smaller than +θ to +θ, the intensities of reflected signals increase until the steer angle becomes +θ. FIG. 6B is a view illustrating the intensities of reflected signals from a non-facing target and steer angles in the same plane. Also, in the example of FIG. 6B, the angle θ is larger than 15°.

Also, in FIG. 6B, a case where the inclination angle of the reflecting surface of the target relative to the direction of the transmission beam is +θ is shown as an example, and for example, in a case where the inclination angle of the reflecting surface of the target relative to the direction of the transmission beam is −θ, on the contrary to the above description, as the steer angle gradually decreases from an angle larger than −θ to −θ, the intensities of reflected signals gradually increase until the steer angle becomes −θ.

Speckle noise is noise which is generated if ultrasonic beams are scattered at boundary surfaces and the like in a subject body and the scattered beams interfere each other. Therefore, the signal intensities of reflected signals including speckle noise do not depend on the steer angle, as shown in FIG. 6C. FIG. 6C is a view illustrating the signal intensities of reflected signals including speckle noise and steer angles in the same plane.

The regression estimate generating unit 16 performs regression analysis on the basis of the relation between steer angles and the intensities of reflected signals as described above. Specifically, the regression estimate generating unit 16 performs regression analysis based on pixel values (luminance values) corresponding to the intensities of reflected signals, on a plurality of ultrasound data items generated by the image generating unit 14 and corresponding to a plurality of steer angles, for each of pixels or each of predetermined areas. The predetermined areas are, for example, areas each of which is composed of a predetermined number of pixels and which are adjacent to one another, or areas defined by division based on the magnitudes of pixel values (luminance values) and adjacent to one another. The predetermined areas may meet, for example, at an area composed of one pixel.

Hereinafter, a regression estimate calculation method in a case where the regression estimate generating unit 16 uses single regression analysis will be described.

Figure 7A:
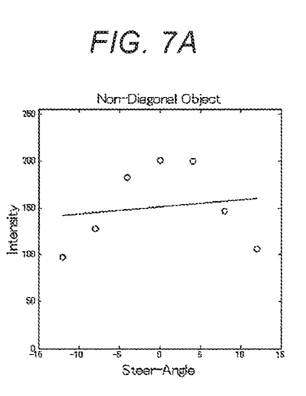
FIG. 7A is a view illustrating an example of a primary regression equation in a case of a facing target.
Figure 7B:
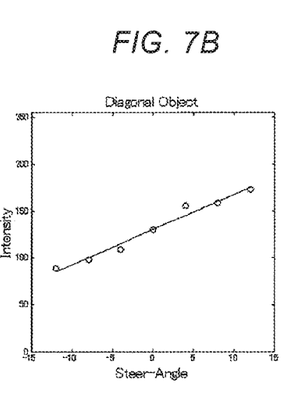
FIG. 7B is a view illustrating an example of a primary regression equation in a case of a non-facing target.
Figure 7C:
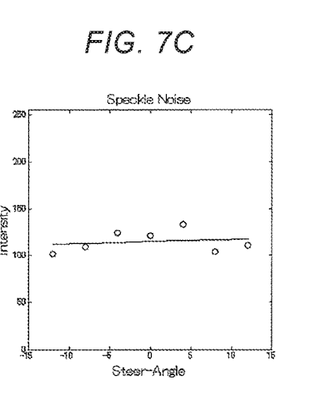
FIG. 7C is a view illustrating an example of a primary regression equation in a case of speckle noise.

For example, primary regression equations which can be obtained on the basis of the relations between intensities of reflected signals and steer angles corresponding to the facing target, the non-facing target, and the speckle noise and shown in FIGS. 6A to 6C by single regression analysis are shown as examples in FIGS. 7A to 7C. As parameters which can be obtained by such regression analysis, for example, there are parameters shown in the following Table 1. Table 1 is a table showing the relation of the magnitudes of various parameters which can be obtained by single regression analysis.

TABLE 1

|  | $|a_1|$ | $a_0$ | RSS | $R^2$ |
| --- | --- | --- | --- | --- |
| Facing Target | Small | Medium | Large | Small |
| Non-facing Target | Large | Small | Small | Large |
| Speckle Noise | Small | Small | Small | Large |

In Table 1, $a_1$ represents the inclination of a primary regression equation calculated by regression analysis, and $a_0$ represents the intercept of a primary regression equation calculated by regression analysis, and RSS represents a residual sum of squares, and $R^2$ represents a determination coefficient. In other words, a primary regression equation can be expressed as $y=a_1x+a_0$. RSS is the sum of squares of the differences at individual points between actual measurement values and an estimation model, and is an evaluation measure of mismatch between the actual measurement values and the estimation model. Also, $R^2$ is a measure of the accuracy of regression analysis.

As shown in FIG. 7A and Table 1, the facing target has the magnitude of the inclination $|a_1|$ of the primary regression equation smaller than that of the non-facing target, and has the magnitude of the intercept $a_0$ larger than that of the non-facing target. As shown in FIG. 7B, the non-facing target has the magnitude of the inclination $|a_1|$ of the primary regression equation larger than those of the other target and the speckle noise. As shown in FIG. 7C, since the speckle noise has random values with respect to signal intensities, the speckle noise has the magnitude of the inclination $|a_1|$ of the primary regression equation smaller than that of the non-facing target.

The regression estimate generating unit 16 calculates regression estimates α on the basis of the parameters (the inclination $|a_1|$, the intercept $a_0$, RSS, $R^2$, and the like of each primary regression equation) obtained by such regression analysis by the following calculation method, and outputs the regression estimates to the image synthesis unit 17.

Also, in the present invention, the regression estimates α are weighting values for performing weighting such that weights for pixel values of areas corresponding to non-facing targets are heavy and weights for pixel values of the other areas are light. Therefore, the regression estimate generating unit 16 determines regression estimates α such that regression estimates α for pixel values of areas corresponding to non-facing targets are large and regression estimates α for pixel values of the other areas are small.

The calculation of regression estimates α which is performed by the regression estimate generating unit 16 may be performed, for example, using any one of expressions to be shown as examples below.

(First Method of Calculating Regression Estimates α)

$$\alpha = |a_1| \quad (1)$$

(Second Method of Calculating Regression Estimates α)

$$\alpha = |a_1| \cdot \gamma \quad (2)$$

Here, γ is a predetermined coefficient.

(Third Method of Calculating Regression Estimates α)

$$\alpha = \frac{|a_1|}{RSS} \quad (3)$$

(Fourth Method of Calculating Regression Estimates α)

$$\alpha = |a_1| \cdot (RSS_{max} - RSS) \quad (4)$$

(Fifth Method of Calculating Regression Estimates α)

$$\alpha = |a_1| \cdot R^2 \quad (5)$$

In the present embodiment, as the method of calculating regression estimates α which is performed by the regression estimate generating unit 16, five deriving methods of Expressions (1) to (5) have been taken as examples. However, the present invention is not limited thereto, and other deriving methods may be used. As described above, the regression estimate generating unit 16 may determine regression estimates α such that regression estimates α for areas corresponding to non-facing targets are large and regression estimates α for the other areas are small. Also, the regression estimate generating unit 16 may perform a normalization process, a clipping process, and the like such that regression estimates α fall in a range between 0 and 1.

Now, an image synthesizing process which the image synthesis unit 17 performs using the regression estimates α calculated by the regression estimate generating unit 16 will be described.

The image synthesis unit 17 synthesizes pixel values (luminance values) of a plurality of ultrasound image data items generated on the basis of reflected signals of ultrasonic beams at different steer angles by the image generating unit 14, with respect to each of pixels or each of predetermined areas, in the following manner, thereby synthesizing the plurality of ultrasound image data items.

(First Image Synthesis Method)

In a first image synthesis method, the image synthesis unit 17 performs α blending on the pixel values of the plurality of ultrasound image data items with respect to each predetermined area, using the absolute values |α| of the regression estimates α. For example, a synthesis expression in a case of using five ultrasound image data items A to E becomes the following Expression (6).

$$\text{Data} = |\alpha| * f_1(A,B,C,D,E) + (1-|\alpha|) * f_2(A,B,C,D,E) \quad (6)$$

Here, in Expression (6), f1 and f2 are predetermined functions. As the functions f1 and f2, for example, any one of a MEAN function for obtaining the simple mean of parameters, a MAX function for extracting a maximum value, a MIN function for extracting a minimum value, a MEDIAN function for extracting a median value, a VARIANCE function for obtaining a variance value, an SD function for obtaining a standard deviation, a Weighted-MEAN function for obtaining a weighted mean, and the like may be used.

A function to be used by the image synthesis unit 17 may be appropriately selected, for example, according to the deriving method used to generate the regression estimates α by the regression estimate generating unit 16, the purpose of use of an ultrasound image to be finally generated by the ultrasonic diagnostic apparatus 100, and so on. Also, this selection may be performed by an operation of a user (such as a doctor) of the ultrasonic diagnostic apparatus 100 on the operation input unit 11, or may be automatically performed, for example, by the control unit 19 of the ultrasonic diagnostic apparatus 100. The functions $f_1$ and $f_2$ may be the same, or may be different functions.

(Second Image Synthesis Method)

In a second image synthesis method, the image synthesis unit 17 synthesizes pixel values of the plurality of ultrasound image data items with respect to each predetermined area, using the regression estimates α generated by the regression estimate generating unit 16 and a predetermined coefficient β.

$$\text{Data}=|\alpha|*f_1(A,B,C,D,E)+\beta*f_2(A,B,C,D,E) \quad (7)$$

In Expression (7), the predetermined coefficient β may be arbitrarily set, for example, by an operation of the user (such as a doctor) of the ultrasonic diagnostic apparatus 100 on the operation input unit 11, or may be automatically determined by the control unit 19, or may be a predetermined fixed value. In a case where the control unit 19 automatically determines the functions $f_1$ and $f_2$ and the predetermined coefficient β, the user of the ultrasonic diagnostic apparatus 100 can obtain an appropriate synthetic image data item without making an effort to determine the functions and the coefficient and to perform an operation. In a case where the user arbitrarily determines the functions $f_1$ and $f_2$ and the predetermined coefficient β, the user can appropriately adjust the display state of an image according to the purpose.

According to the image synthesis method as described above, the image synthesis unit 17 can perform weighting such that weights for areas corresponding to non-facing targets become relatively heavy and weights for the other areas become light, and synthesize the plurality of ultrasound image data items.

As described above, the ultrasonic diagnostic apparatus 100 of the present invention includes the image generating unit 14 configured to generate a plurality of different ultrasound image data items from reception signals corresponding to a plurality of different steering angles, respectively, on the basis of the reception signals which the ultrasound probe 2 has generated on the basis of reflected ultrasonic waves received from a reflecting surface of a subject body by transmitting ultrasonic waves at the plurality of different steering angles, and the regression estimate generating unit 16 configured to perform regression analysis on the basis of the plurality of different steering angles and the plurality of ultrasound image data items corresponding to the plurality of different steering angles, and generate regression estimates which are predetermined weighting values on the basis of the result of the regression analysis, and the image synthesis unit 17 configured to perform weighting on the plurality of ultrasound image data items on the basis of the regression estimates, and synthesize them, thereby generating a synthetic image data item.

The regression estimate generating unit 16 performs regression analysis on the ultrasound image data items with respect to each pixel or each predetermined area, on the basis of pixel values (luminance values), thereby calculating the regression estimates α such that relative weights for targets (non-facing targets) having reflecting surfaces inclined with respect to the transmission beam become heavy. Therefore, the image synthesis unit 17 can perform weighting such that relative weights for areas corresponding to non-facing targets become heavy and relative weights for the other areas become relatively light, and generate a synthetic image data item. Therefore, the ultrasonic diagnostic apparatus 100 of the present invention can generate a synthetic image data item in which non-facing targets are relatively clear, as compared to a case where such weighting is not performed.

Although the embodiment of the present invention has been described with reference to the drawings, the present invention is not limited to the related examples. Various alterations or modifications which can be devised within the scope as set forth in the claims by those skilled in the art are also included in the technical scope of the present invention. Also, the individual components of the above-described embodiment may be arbitrarily combined without departing from the gist of the disclosure.

In the above-described embodiment, the plurality of vibrators 2a of the ultrasound probe 2 is arranged in a one-dimensional array in the azimuth direction (the scan direction). However, they may be arranged in a two-dimensional array. Also, in the above-described embodiment, a linear scanning type electronic scanning probe is used as the ultrasound probe 2 to perform ultrasound scanning using a linear scanning method. However, other types such as a sector scanning type and a convex scanning type can also be used.

In the above-described embodiment, the regression estimate generating unit 16 generates regression estimates by single regression analysis. However, the present invention is not limited thereto. For example, the regression estimate generating unit 16 may generate a quadratic regression equation or perform other regression analysis.

Figure 8A:
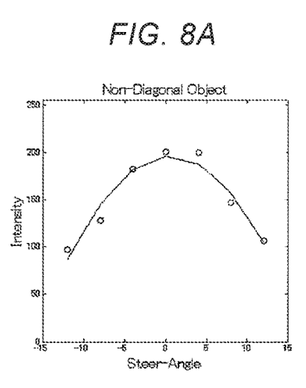
FIG. 8A is a view illustrating an example of a quadratic regression equation in a case of a facing target.
Figure 8B:
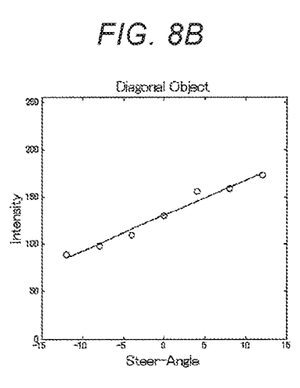
FIG. 8B is a view illustrating an example of a quadratic regression equation in a case of a non-facing target.
Figure 8C:
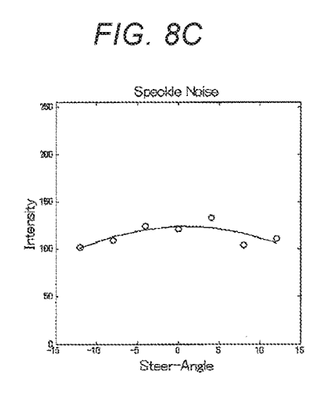
FIG. 8C is a view illustrating an example of a quadratic regression equation in a case of speckle noise.

Hereinafter, a case where the regression estimate generating unit 16 generates a quadratic regression equation will be described. FIGS. 8A to 8C are view illustrating examples of quadratic regression equations, i.e. $y=a_2x^2+a_1x+0$ which can be obtained on the basis of the relations between intensities of reflected signals and steer angles corresponding to the facing target, the non-facing target, and the speckle noise as shown in FIGS. 6A to 6C by regression analysis.

As shown in FIGS. 8A and 8C, relational expressions between the intensities of reflected signals and steer angles corresponding to the facing target and the speckle noise represent relations close to quadratic curves. However, as shown in FIG. 8B, a relational expression between the intensities of reflected signals and steer angles corresponding to the non-facing target is represented as a linear line substantially straight, similarly in a case of a primary regression equation. Therefore, parameters which can be obtained by quadratic regression analysis have a magnitude relation as shown in the following Table 2.

TABLE 2

|  | $|a_2|$ | $|a_1|$ | $a_0$ | RSS | $R^2$ |
|---|---|---|---|---|---|
| Facing Target | Small | Small | Medium | Small | Large |
| Non-facing Target | Large | Large | Small | Small | Large |
| Speckle noise | Medium | Small | Small | Small | Medium |

Like this, even in a case where the parameters are obtained by quadratic regression analysis, coefficients (parameters $|a_2|$ and $|a_1|$) of independent variables corresponding to the non-facing target are larger than coefficients corresponding to the facing target and the speckle noise. Therefore, the regression estimate generating unit 16 can determine regression estimates α on the basis of the parameters $|a_2|$ and $|a_1|$ such that regression estimates α for areas corresponding to non-facing targets are large and regression estimates α for the other areas are small.

The present invention is suitable for an ultrasonic diagnostic apparatus for synthesizing images on the basis of reflected signals of ultrasonic transmission beams at a plurality of steer angles.

According to an embodiment, it is possible to provide an ultrasonic diagnostic apparatus and an image synthesis method capable of appropriately generating ultrasound images including body tissues which do not face an ultrasound probe.

Although embodiments of the present invention have been described and illustrated in detail, it is clearly understood that the same is by way of illustration and example only and not limitation, the scope of the present invention should be interpreted by terms of the appended claims.

What is claimed is:

1. An ultrasonic diagnostic apparatus comprising:
an image generating unit configured to generate a plurality of different ultrasound image data items corresponding to a plurality of different steering angles, respectively, on the basis of reception signals which an ultrasound probe has generated on the basis of reflected ultrasonic waves received from a reflecting surface of a subject body by transmitting ultrasonic waves at the plurality of different steering angles, wherein a first steering angle of the plurality of different steering angles sets a transmission direction perpendicular to an azimuth direction of the ultrasound probe, and the plurality of different steering angles further includes at least one pair of steering angles shifted in the azimuth direction on opposing sides of the first steering angle by a predetermined angle
a regression estimate generating unit configured to perform regression analysis on the basis of the plurality of different steering angles and the plurality of ultrasound image data items corresponding to the plurality of different steering angles, obtain a coefficient of a regression equation as a result of performing the regression analysis, and generate regression estimates which are predetermined weighting values as functions of the coefficient of the regression equation obtained by the regression analysis; and
an image synthesis unit configured to perform weighting on the plurality of ultrasound image data items on the basis of the regression estimates, and synthesize the plurality of ultrasound image data items, thereby combining the plurality of ultrasound image data items to generate a synthetic image data item, wherein the image synthesis unit performs $\alpha$ blending on the plurality of ultrasound image data items according to the expression:

$$\text{Data}=|\alpha|*f_1(I_1\text{-}I_n)+(1-|\alpha|)*f_2(I_1\text{-}I_n); \text{ or}$$

$$\text{Data}=|\alpha|*f_1(I_1\text{-}I_n)+\beta*f_2(I_1\text{-}I_n),$$

where $f_1$, $f_2$ are predetermined functions, $I_1\text{-}I_n$ are pixel values of n ultrasound image data items, $\alpha$ is the regression estimate, and $\beta$ is a predetermined coefficient.

2. The ultrasonic diagnostic apparatus according to claim 1, wherein:
the regression estimate generating unit uses the regression analysis to generate the regression estimates such that the predetermined weighting values for areas of the ultrasound image data items corresponding to tissues in the subject body having reflecting surfaces inclined with respect to a transmission direction of the ultrasonic waves become relatively large and the predetermined weighting values for other areas become relatively small.

3. The ultrasonic diagnostic apparatus according to claim 1, wherein:
the regression analysis performed by the regression estimate generating unit is a single regression analysis and the regression estimates are inclinations of primary regression equations obtained by the single regression analysis.

4. The ultrasonic diagnostic apparatus according to claim 1, wherein:
the image synthesis unit performs a blending on the plurality of ultrasound image data items according to the expression:

$$\text{Data}=|\alpha|*f_1(I_1\text{-}I_n)+(1-|\alpha|)*f_2(I_1\text{-}I_n),$$

where $f_1$, $f_2$ are predetermined functions, $I_1\text{-}I_n$ are pixel values of n ultrasound image data items, and $\alpha$ is the regression estimate.

5. The ultrasonic diagnostic apparatus according to claim 1, wherein:
the image synthesis unit performs a blending on the plurality of ultrasound image data items according to the expression:

$$\text{Data}=|\alpha|*f_1(I_1\text{-}I_n)+\beta*f_2(I_1\text{-}I_n),$$

where $f_1$, $f_2$ are predetermined functions, $I_1\text{-}I_n$ are pixel values of n ultrasound image data items, $\alpha$ is the regression estimate, and $\beta$ is a predetermined coefficient.

6. The ultrasonic diagnostic apparatus according to claim 4, wherein:
the first function and the second function are functions for obtaining any one value of a mean value, a maximum value, a minimum value, a median value, a variance, and a standard deviation with respect to input values.

7. The ultrasonic diagnostic apparatus according to claim 1, wherein:
the regression estimates are further based on a residual sum of squares.

8. The ultrasonic diagnostic apparatus according to claim 1, wherein:
the regression estimates are further based on a determination coefficient.

9. An image synthesis method of an ultrasonic diagnostic apparatus comprising:
based on reception signals which an ultrasound probe has generated on a basis of reflected ultrasonic waves received from a reflecting surface of a subject body by transmitting ultrasonic waves at a plurality of different steering angles, generating a plurality of ultrasound image data items from the reception signals corresponding to the plurality of different steering angles, respectively, wherein a first steering angle of the plurality of different steering angles sets a transmission direction perpendicular to an azimuth direction of the ultrasound probe, and the plurality of different steering angles further includes at least one pair of steering angles shifted in the azimuth direction on opposing sides of the first steering angle by a predetermined angle
performing regression analysis on the basis of the plurality of different steering angles and the plurality of ultrasound image data items corresponding to the plurality of different steering angles, wherein a coefficient of a regression equation is obtained by the regression analysis;
generating regression estimates which are predetermined weighting values based on the coefficient of the regression equation obtained by the regression analysis; and performing weighting on the plurality of ultrasound image data items based on the regression estimates, and synthesizing the plurality of ultrasound image data items, thereby combining the plurality of ultrasound image data items to generate a synthetic image data item, wherein the image synthesis unit performs a blending on the plurality of ultrasound image data items according to the expression:

$$Data = |\alpha| * f_1(I_1 - I_n) + (1 - |\alpha|) * f_2(I_1 - I_n); \text{ or}$$

$$Data = |\alpha| * f_1(I_1 - I_n) + \beta * f_2(I_1 - I_n),$$

where $f_1$, $f_2$ are predetermined functions, $I_1$-$I_n$, are pixel values of n ultrasound image data items, $\alpha$ is the regression estimate, and $\beta$ is a predetermined coefficient.

10. An ultrasonic diagnostic apparatus comprising:

an image generating unit configured to generate a plurality of different ultrasound image data items corresponding to a plurality of different steering angles, respectively, on the basis of reception signals which an ultrasound probe has generated on the basis of reflected ultrasonic waves received from a reflecting surface of a subject body by transmitting ultrasonic waves at the plurality of different steering angles, wherein a first steering angle of the plurality of different steering angles sets a transmission direction perpendicular to an azimuth direction of the ultrasound probe, and the plurality of different steering angles further includes at least one pair of steering angles shifted in the azimuth direction on opposing sides of the first steering angle by a predetermined angle a regression estimate generating unit configured to perform regression analysis on the basis of the plurality of different steering angles and the plurality of ultrasound image data items corresponding to the plurality of different steering angles, obtain at least one parameter as a result of performing the regression analysis from the group of parameters consisting of a coefficient of a regression equation, a residual sum of squares, and a determination coefficient, and generate regression estimates which are predetermined weighting values as functions of the at least one parameter obtained by the regression analysis; and an image synthesis unit configured to perform weighting on the plurality of ultrasound image data items on the basis of the regression estimates, and synthesize the plurality of ultrasound image data items, thereby combining the plurality of ultrasound image data items to generate a synthetic image data item, wherein the image synthesis unit performs $\alpha$ blending on the plurality of ultrasound image data items corresponding to the plurality of steering angles with respect to each of predetermined areas according to the expression:

$$Data = |\alpha| * f_1(I_1 - I_n) + (1 - |\alpha|) * f_2(I_1 - I_n); \text{ or}$$

$$Data = |\alpha| * f_1(I_1 - I_n) + \beta * f_2(I_1 - I_n),$$

where $f_1$, $f_2$ are predetermined functions, $I_1$-$I_n$ are pixel values of n ultrasound image data items, $\alpha$ is the regression estimate, and $\beta$ is a predetermined coefficient.

* * * * *